United States Patent [19]
Nabeshima et al.

[11] Patent Number: 6,107,330
[45] Date of Patent: Aug. 22, 2000

[54] INHIBITOR FOR NARCOTIC ANALGESIC DEPENDENCE/RESISTANCE ACQUISITION

[75] Inventors: Toshitaka Nabeshima, Aichi; Mitsunobu Yoshii; Tadashi Shiotani, both of Tokyo, all of Japan

[73] Assignee: Daiichi Pharmaceutical Co., Ltd., Tokyo, Japan

[21] Appl. No.: 09/000,236

[22] PCT Filed: Aug. 6, 1995

[86] PCT No.: PCT/JP96/02207

§ 371 Date: Mar. 19, 1998

§ 102(e) Date: Mar. 19, 1998

[87] PCT Pub. No.: WO97/06139

PCT Pub. Date: Feb. 20, 1997

[30] Foreign Application Priority Data

Aug. 7, 1995 [JP] Japan .................................. 7-200763

[51] Int. Cl.$^7$ ............................ A61K 31/40; A61K 31/44
[52] U.S. Cl. ............................................ 514/424; 514/343
[58] Field of Search ...................... 514/424, 343

[56] References Cited

U.S. PATENT DOCUMENTS

| | | |
|---|---|---|
| 4,212,878 | 7/1980 | Lednicer et al. . |
| 4,341,790 | 7/1982 | Betzing et al. . |
| 4,380,550 | 4/1983 | Kleinlogel et al. . |
| 5,185,329 | 2/1993 | Gawin et al. . |
| 5,220,018 | 6/1993 | Bock et al. . |
| 5,461,157 | 10/1995 | Kamihara et al. . |
| 5,468,749 | 11/1995 | Gawin et al. . |

FOREIGN PATENT DOCUMENTS

| | | |
|---|---|---|
| 893276 | 11/1982 | Belgium . |
| 0356997 | 3/1990 | European Pat. Off. . |
| 0415693 | 3/1991 | European Pat. Off. . |
| 0508796 | 10/1992 | European Pat. Off. . |
| 56-29560 | 1/1981 | Japan . |
| 2209808 | 8/1990 | Japan . |
| 3163030 | 7/1991 | Japan . |
| 6-65197 | 3/1994 | Japan . |
| 6-87838 | 3/1994 | Japan . |

OTHER PUBLICATIONS

Chemical Abstracts, vol. 121, No. 13, Sep. 26, 1994, Abstract No. 148985, XP002077188.

Database WPI, Week 9309, Derwent Publications Ltd., London, GB, AN 93–071079, XP002077191, 1993.

Chemical Abstracts, vol. 86, No. 14, Apr. 4, 1997, Abstract No. 95989, XP002077189.

Chemical Abstracts, vol. 119, No. 5, Aug. 2, 1993, Abstract No. XP002077190.

*Primary Examiner*—William R. A. Jarvis
*Attorney, Agent, or Firm*—Greenblum & Bernstein, P.L.C.

[57] ABSTRACT

A medicament which comprises as an active ingredient a compound represented by the following formula: $R^2\text{-CH}_2\text{CONH-}R^1$ wherein $R^1$ represents a pyridyl group, a substituted pyridyl group, phenyl group, or a substituted phenyl group; and $R^2$ represents 2-oxo-1-pyrrolidinyl group which may optionally be substituted, and inhibits the development of dependency induced by a narcotic analgesic and/or inhibit the development of tolerance to analgesic action induced by a narcotic analgesic agent.

26 Claims, No Drawings

INHIBITOR FOR NARCOTIC ANALGESIC DEPENDENCE/RESISTANCE ACQUISITION

This application is a 371 PCT/SP96/02207, filed Aug. 6, 1996.

TECHNICAL FIELD

The present invention relates to a medicament for inhibiting developments of dependency and tolerance to analgesic action which are induced by the administration of a narcotic analgesic agent.

BACKGROUND ART

Narcotic analgesic agents, e.g., morphine, have excellent analgesic action against visceral pains or other, and are clinically used for alleviation of pain for terminal cancer patients. However, the narcotic analgesic agents are typical drugs that affect on mental functions and develop psychic and physical dependency. In addition, tolerance to analgesic action, as being their primary efficacy, is rapidly developed by repeated administrations. Accordingly, carefully controlled frequency of administration and dose are required to achieve a desired analgesic action, while maintaining minimized development of dependency.

Therefore, when a narcotic analgesic agent such as morphine is used, it is necessary to inhibit the development of tolerance to analgesic activity without reducing analgesic activity to meet the purpose of the use. It is also important to inhibit the development of dependency.

An object of the present invention is to provide a medicament having inhibitory activity against the development of dependency induced by the administration of the narcotic analgesic agent such as morphine. Another object of the present invention is to provide a medicament having inhibitory activity against the development of tolerance to analgesic action induced by the administration of the narcotic analgesic agent such as morphine. A further object of the present invention is to provide a medicament having both of the aforementioned pharmacological activities.

DISCLOSURE OF THE INVENTION

The inventors of the present invention conducted various studies to achieve the foregoing objects, and as a result, they found that 2-(1-pyrrolidinyl)acetamide derivatives, which are useful as medicaments for improving cerebral functions, have the aforementioned pharmacological activities. They also found that the derivatives are useful as active ingredients of medicaments which inhibit the developments of dependency and/or the developments of tolerance to analgesic actions induced by narcotic analgesic drugs. The present invention was achieved on the basis of these findings.

The present invention thus provides a medicament which comprises as an active ingredient a compound represented by the following formula: $R^2\text{-}CH_2CONH\text{-}R^1$ wherein $R^1$ represents a pyridyl group, a substituted pyridyl group, phenyl group, or a substituted phenyl group; and $R^2$ represents 2-oxo-1-pyrrolidinyl group which may optionally be substituted, and inhibits the development of dependency induced by a narcotic analgesic agent and/or inhibits the development of tolerance to analgesic action induced by a narcotic analgesic agent.

According to preferred embodiments of the present invention, the following inventions are provided: the aforementioned medicament which inhibits the development of dependency induced by a narcotic analgesic agent, and also inhibits the development of tolerance to analgesic action induced by a narcotic analgesic agent; the aforementioned medicament which inhibits the development of dependency induced by a narcotic analgesic agent; the aforementioned medicament which inhibits the development of tolerance to analgesic action induced by a narcotic analgesic agent; the aforementioned medicament used in combination with a narcotic analgesic agent; the aforementioned medicament having a prophylactic effect to reduce or prevent the development of dependency induced by a narcotic analgesic agent and/or the development of tolerance to analgesic action induced by a narcotic analgesic agent; the aforementioned medicament having a therapeutic effect to reduce or eliminate dependency already developed by a narcotic analgesic agent and/or tolerance to analgesic action already developed by a narcotic analgesic agent; the aforementioned medicament wherein said active ingredient is N-(2,6-dimethylphenyl)-2-(2-oxo-1-pyrrolidinyl)acetamide; the aforementioned medicament wherein said narcotic analgesic agent is morphine hydrochloride or morphine nitrate; and the aforementioned medicament which is in the form of a pharmaceutical composition comprising said active ingredient together with one or more pharmaceutically acceptable additives.

According to another aspect of the present invention, there is also provided an inhibitory agent against the development of dependency and/or against the development of tolerance to analgesic action induced by a narcotic analgesic agent, which comprises as an active ingredient a compound represented by the following formula: $R^2\text{-}CH_2CONH\text{-}R^1$ wherein $R^1$ represents a pyridyl group, a substituted pyridyl group, phenyl group, or a substituted phenyl group; and $R^2$ represents 2-oxo-1-pyrrolidinyl group which may optionally be substituted. According to preferred embodiments of this invention, there are provided the inhibitory agent against the development of dependency induced by a narcotic analgesic agent; and the inhibitory agent against the development of tolerance to analgesic action induced by a narcotic analgesic agent.

According to further aspect of the present invention, there is provided a use of a compound represented by the following formula: $R^2\text{-}CH_2CONH\text{-}R^1$ wherein $R^1$ represents a pyridyl group, a substituted pyridyl group, phenyl group, or a substituted phenyl group; and $R^2$ represents 2-oxo-1-pyrrolidinyl group which may optionally be substituted, for the manufacture of a medicament which comprises said compound as an active ingredient and inhibits the development of dependency induced by a narcotic analgesic agent and/or inhibits the development of tolerance to analgesic action induced by a narcotic analgesic agent, preferably for the manufacture of a medicament in the form of a pharmaceutical composition comprising said active ingredient together with one or more pharmaceutically acceptable additives.

In addition to the aforementioned inventions, there is also provided a method for inhibiting the development of dependency induced by a narcotic analgesic agent and/or inhibiting the development of tolerance to analgesic action induced by a narcotic analgesic agent, which comprises the step of administering to a patient a therapeutically and/or preventively effective amount of a compound represented by the following formula: $R^2\text{-}CH_2CONH\text{-}R^1$ wherein $R^1$ represents a pyridyl group, a substituted pyridyl group, phenyl group, or a substituted phenyl group; and $R^2$ represents 2-oxo-1-pyrrolidinyl group which may optionally be substituted.

BEST MODE FOR CARRYING OUT THE INVENTION

The active ingredients of the medicament of the present invention, i.e., the aforementioned 2-(1-pyrrolidinyl) acetamide derivatives, are disclosed in the Japanese Patent Unexamined Publication (KOKAI) No. (Sho) 56-2960/1981 (the U.S. Pat. No. 4,341,790) as compounds useful for improving cerebral functions. $R^1$ represents a pyridyl group, a substituted pyridyl group, phenyl group, or a substituted phenyl group. Examples of one or more substituents on the ring that constitutes the substituted pyridyl group or the substituted phenyl group include, for example, a halogen atom, trifluoromethyl group, nitro group, acetyl group, an alkyl group, an alkoxy group, an alkylmercapto group, amino group, sulfonyl group, and aminoethoxycarbonyl group.

$R^2$ represents 2-oxo-1-pyrrolidinyl group which may optionally be substituted. As a substituent, for example, hydroxyl group may be used. The aforementioned compounds can be readily prepared according to the methods described in the Japanese Patent Unexamined Publication (KOKAI) Nos. (Sho) 56-2960/1981 and (Hei) 6-65197/1994 (the U.S. Pat. Nos. 4,341,790 and 5,461,157, respectively). Among the compounds described above, an example of the most preferred compound includes N-(2,6-dimethylphenyl)-2-(2-oxo-1-pyrrolidinyl)acetamide.

The medicament of the present invention has inhibitory activity against the development of dependency induced by a narcotic analgesic agent, and/or inhibitory activity against the development of tolerance to analgesic action induced by a narcotic analgesic agent. The medicament of the present invention is characterized to exhibit the above-described activities without reducing the analgesic action of a narcotic analgesic agent.

Generally, by using the medicament of the present invention in combination with a narcotic analgesic agent, the medicament can reduce or prevent the development of dependency induced by the narcotic analgesic agent, and also can reduce or prevent the development of tolerance to analgesic action induced by the narcotic analgesic agent. Accordingly, the medicament of the present invention may be used for a prophylactic purpose to reduce or prevent the aforementioned development of dependency and/or development of tolerance. In addition, the medicament of the present invention has reducing and eliminating activity on dependency already developed by the administration of a narcotic analgesic agent or tolerance to analgesic action of the narcotic analgesic agent. Therefore, the medicament of the present invention can be used for a therapeutic purpose to reduce or eliminate the aforementioned already developed dependency and/or tolerance, while generally maintaining a combined administration with a narcotic analgesic agent.

The narcotic analgesic agents are not particularly limited so far as the agents are recognized to develop dependency by a single administration or repeated administrations for a short or prolonged period of time, and/or substantially develop tolerance to analgesic action thereof by repeated administrations for a short or prolonged period of time. Examples of the narcotic analgesic agents include, for example, morphines and their semi-synthesized derivatives derived from opium and non-natural compounds having morphine-like activity such as petidine; and salts of these compounds.

More specifically, examples of the narcotic analgesic agents include, for example, alkaloids obtained from opium and their semi-synthesized derivatives such as, for example, phenanthrenes such as morphine, oxymolphone, hydromolphone, codeine, hydrocodeine, heroin, thebaine, and buprenorphine; phenylpiperidines such as meperidine and fentanyl; phenylheptylamines such as methadone and propoxyphene; morphinans such as levorphanol, methorphan, and levorphane; and benzomorphans such as phenazocine and pentazocine.

Examples also include analgesic peptides as endogenous morphine-like substances such as, for example, enkephalins such as methionine enkephalin and leucine enkephalin; endorphins such as α-endorphin, β-endorphin, and γ-endorphin; and dynorphins such as dynorphin A and dynorphin B, and precursors thereof whose examples include proenkephalins such as proenkephalins, propiomelanocortins, and prodynorphins.

Opiate receptors on which narcotic analgesic agents can act as agonists or antagonists are generally classified into three subclasses, i.e., μ, κ, and δ. Among the narcotic analgesic agents, the medicament of the present invention may preferably be applied to those can act as agonists (or partial agonists) of μ, κ and/or δ receptors. For example, typical narcotic analgesic agents can be classified into the following groups from a viewpoint of their actions on the receptors: morphine, dynorphin B, β-endorphin or other, for example, which acts as an agonist on μ receptor involved in functions leading to analgesic action, miosis, respiratory suppression, euphoria, and dependency at spinal leve; pentazocine or morphine, for example, which acts as an agonist of κ receptor involved in analgesic action, sedation, and miosis at spinal level; and dynorphin A or β-endorphin, for example, which acts as an agonist of δ receptor involved in affective expression.

Although not intended to be bound by any specific theory, narcotic analgesic agents such as morphine are known to decrease the inflow of calcium ions into neurons, and therefore, it can be elucidated that the medicament of the present invention activates the calcium ion channel, and thereby inhibit the development of dependency and the development of tolerance to analgesic action induced by a narcotic analgesic agent.

Route of administration of the medicament of the present invention is not particularly limited, and the medicament can be administered orally and parenterally to humans. The compounds of the aforementioned formula, per se, may be used as the medicament of the present invention. However, it is generally preferable that the medicament is provided as a pharmaceutical composition in a form of formulation well known to one of ordinary skilled in the art, by optionally adding one or more pharmacologically and pharmaceutically acceptable additives to the aforementioned compound as an active ingredient. The medicament of the present invention may generally be administered separately from a narcotic analgesic agent by simultaneously using a narcotic analgesic agent which, per se, is provided in a form of pharmaceutical formulation such as a solution or a tablet.

Methods for the combined administration are not particularly limited. For example, a method comprising the step of continued administrations of the medicament of the present invention in accord with the entire administration period of a narcotic analgesic agent; a method comprising the step of the administration of the medicament of the present invention in need during the administration period of a narcotic analgesic agent; a method comprising the steps of the administration of the medicament of the present invention started prior to the administration of a narcotic analgesic agent, followed by continued combined administrations of a narcotic analgesic agent and the medicament of the present invention; and a method comprising the steps of continued combined administration of a narcotic analgesic agent and the medicament of the present invention, followed by continued and sole administration of the medicament of the present invention after the termination of the administration of the narcotic analgesic agent. If desired, a pharmaceutical composition comprising a narcotic analgesic agent and the medicament of the present invention (so called "a formulation comprising multiple active ingredients") may be prepared and administered.

Examples of the pharmaceutical compositions suitable for oral administration include, for example, tablets, capsules, powders, subtilized granules, granules, solutions, and syrups. Examples of the pharmaceutical compositions suitable for parenteral administration include, for example, injections for subcutaneous, intravenous, and intramuscular injections, drip infusions, suppositories, inhalants, transdermal preparations, transmucosal preparations, and patches. Examples of the pharmacologically and pharmaceutically acceptable additives include, for example, excipients, disintegrators or disintegrating aids, binders, lubricants, coating agents, coloring agents, diluents, base materials, solubilizers or solubilizing aids, isotonicities, pH modifiers, stabilizers, propellants, and adhesives.

For example, as pharmacologically or pharmaceutically acceptable additives for the manufacture of pharmaceutical compositions suitable for oral, transdermal, or transmucosal administration, pharmaceutical additives such as, for example, excipients such as glucose, lactose, D-mannitol, starch, and crystalline cellulose; disintegrators or disintegrating aids such as carboxymethylcellulose, starch, and carboxymethylcellulose calcium; binders such as hydroxypropylcellulose, hydroxypropylmethylcellulose, polyvinylpyrrolidone, and gelatine; lubricants such as magnesium stearate and talc; coating agents such as hydroxypropylmethylcellulose, saccharose, polyethylene glycol, and titanium oxide; and base materials such as vaseline, liquid paraffin, polyethylene glycol, gelatin, china clay, glycerin, purified water, and hard fat may be used. Pharmaceutical additives such as propellants such as flons, diethyl ether, and compressed gases; adhesives such as sodium polyacrylate, polyvinyl alcohol, methylcellulose, polyisobutylene, and polybutene; and base cloths such as cotton cloth and plastic sheets may be used for the manufacture of the pharmaceutical compositions.

Pharmaceutical compositions suitable for the use as injections and drip infusions may be added with, for example, solubilizers or solubilizing aids such as distilled water for injection, physiological saline, and propylene glycol which can constitute aqueous injections or injections dissolved before use; isotonicities such as glucose, sodium chloride, D-mannitol, and glycerin; pH modifiers such as inorganic acids, organic acids, inorganic bases, and organic bases.

Doses and dosing period of the medicament of the present invention are not particularly limited and they may suitably be chosen depending on, for example, administration route, a degree of the development of dependency and/or the development of tolerance, purpose of administration such as prophylactic or therapeutic administration, and the age or body weight of a patient. As to examples of the dose, where a narcotic analgesic agent such as morphine hydrochloride, morphine nitrate, or a sustained-release formulation thereof is administered in a dose of from about 10 to 30 mg per day from once to three times a day, the medicament of the present invention may be applied to a combined administration in a dose of, for example, from 200 to 2,000 mg, preferably from 300 to 900 mg per day as a weight of an active ingredient. The above-described daily dose may be administered several times a day as divided portions. Where the medicament of the present invention is administered repeatedly at a high dose, it is preferable that the dose should be appropriately chosen under the monitor of inhibitory activity against the development of tolerance to analgesic action. As to the dosing period, it is desirable that the medicament of the present invention is administered as long as possible for the entire administration period of a narcotic analgesic agent.

EXAMPLES

The present invention will be explained more specifically by referring to examples. However, the scope of the present invention is not limited to the examples set out below. In the examples, N-(2,6-dimethylphenyl)-2-(2-oxo-1-pyrrolidinyl-acetamide (generic name "nefiracetam," referred to as "the medicament of the present invention" in the examples set out below) was used as the medicament according to the present invention. Each of the medicament of the present invention and morphine was dissolved in physiological saline. Control group was administered only with physiological saline.

Example 1: Effect of the medicament of the present invention on the analgesic action induced by an acute administration of morphine Effects on the analgesic action of morphine and the development of tolerance were studied using ddY male mice according to tail-flick test, one of experimental tests for evaluating analgesic action in which thermal stimulations are applied. The medicament if the present invention (5 or 10 mg/kg) was orally administered to the mice, and the morphine (3 or 6 mg/kg) was subcutaneously administered in their back after 15 minutes. Tail-flick tests were carried out one hour after the morphine administration. Three measurements were performed for each of the mice and an average value was recorded as a result for the mouse. Cut off time of the measurement was adjusted to 10 seconds, and where no tail-flick reaction was observed for 10 seconds or more, tail-flick latency was recorded as 10 seconds.

As shown Table 1, morphine dose-dependently prolonged tail-flick latency and exhibited analgesic action. Pretreatment with the medicament of the present invention 15 minutes prior to the morphine administration did not affect the analgesic action of morphine, and no reduction of the analgesic action of morphine by the medicament of the present invention was observed. In addition, no analgesic action of the medicament of the present invention, per se, was observed. In Table 1, nefiracetam 5 mg/kg, and 10 mg/kg represent the administrations of 5 and 10 mg/kg of the medicament of the present invention, respectively (the same in tables below), and the symbols "a " and "aa" indicate $p<0.05$ and $p<0.01$ v.s. physiological saline (pre-administration+physiological saline (post-administration), respectively.

TABLE 1

| Nefiracetam (mg/kg) | Morphine (mg/kg) | N | Tail-flick latency (second) |
|---|---|---|---|
| 0 | 0 | 9 | 3.97 ± 0.33 |
| 5 | 0 | 9 | 4.41 ± 0.34 |
| 10 | 0 | 9 | 4.21 ± 0.32 |
| 0 | 3 | 9 | 7.09 ± 0.84 a |
| 5 | 3 | 9 | 8.01 ± 0.85 aa |

TABLE 1-continued

| Nefiracetam (mg/kg) | Morphine (mg/kg) | N | Tail-flick latency (second) |
|---|---|---|---|
| 10 | 3 | 9 | 8.09 ± 0.66 aa |
| 0 | 6 | 9 | 9.66 ± 0.23 aa |
| 5 | 6 | 9 | 8.87 ± 0.63 aa |
| 10 | 6 | 9 | 8.67 ± 0.78 aa |

Example 2: Effects of the medicament of the present invention on the development of tolerance to the analgesic action induced by repeated administration of morphine.

After approximately one month of pause of administration of drug from the acute administration test, repeated administration test was started. The medicament of the present invention (5 or 10 mg/kg) was orally administered to the mice, and then the mice were subcutaneously administered with morphine (6 or 20 mg/kg) in their backs after 15 minutes. The drug administrations were carried out twice a day in the morning and evening for 5 days in total. On the 6th day, morphine was administered subcutaneously (6 mg/kg), and one hour after the administration, tail-flick test were performed according to the method described above, except that the cut off of the tail-flick latency was provided for 15 seconds.

As shown in Table 2, shortened tail-flick latencies, i.e., developments of tolerance to analgesic action of morphine, were observed by the repeated administrations of morphine. On the other hand, the development of tolerance induced by the repeated administration of morphine (6 mg/kg) was inhibited by the combined administration of the medicament of the present invention (5 mg/kg). The combined administration of the medicament of the present invention (10 mg/kg) reduced the degree of the development of the tolerance.

In addition, a tendency of reduced tolerance was observed as to the development of tolerance induced by the repeated administration of morphine at a high dose (20 mg/kg). When morphine was administered to mice which had been administered repeatedly with the medicament of the present invention, no effect on the analgesic action of morphine was observed. In Table 2, the symbols represent:

"a" and "aa": $p<0.05$ and $p<0.01$ v.s. control (physiological saline+physiological saline) treatment, respectively;
"b" and "bb": $p<0.05$ and $p<0.01$ v.s. subacute (physiological saline+physiological saline) treatment, and
"cc": $p<0.01$ v.s. subacute (physiological saline+morphine 6 mg/kg) treatment.

TABLE 2

| Nefiracetam (mg/kg) | Morphine 1st to 5th day × 2 (mg/kg) | Morphine 6th day (mg/kg) | N | Tail-flick latency (sec.) |
|---|---|---|---|---|
| (Control) | | | | |
| 0 | 0 | 0 | 7 | 3.70 ± 0.13 |
| (Combined administration group) | | | | |
| 0 | 0 | 6 | 16 | 11.21 ± 0.77 aa |
| 5 | 0 | 6 | 9 | 10.15 ± 1.31 aa |
| 10 | 0 | 6 | 9 | 10.30 ± 1.33 aa |
| 0 | 6 | 6 | 16 | 4.98 ± 0.27 bb |
| 5 | 6 | 6 | 16 | 9.15 ± 1.12 cc |
| 10 | 6 | 6 | 16 | 6.91 ± 0.66 bb |
| 0 | 20 | 6 | 16 | 4.58 ± 0.70 bb |
| 5 | 20 | 6 | 16 | 6.96 ± 0.73 bb |
| 10 | 20 | 6 | 15 | 7.20 ± 0.92 b |
| 20 | 20 | 6 | 14 | 7.10 ± 0.99 b |

Example 3: Effect of the medicament of the present invention on the development of physical dependency induced by repeated administration of morphine The medicament of the present invention was orally administered (5 or 10 mg/kg) to mice, and then morphine was subcutaneously administered in their backs (6 or 20 mg/hg) after 15 minutes. The drug administration was carried out twice a day in the morning and evening for 5 days in total. The same treatment was once performed on the 6th day, and then naloxone was administered (5 mg/kg, i.p.) after two hours.

Withdrawal symptoms induced by the naloxone administration, including jumping, wet dog shake, and diarrhea, were observed for 30 minutes immediately after the naxalone administration. Losses of body weights were also measured. The results are shown in Table 3. In Table 3, the symbols represent: "a" and "aa": $p<0.05$ and $p<0.01$ v.s. subacute (physiological saline+physiological saline) treatment, respectively; "b" and "bb": $p<0.05$ and $p<0.01$ v.s. subacute (physiological saline+morphine 6 mg/kg) treatment, respectively; and "c": $p<0.05$ v.s. subacute (physiological saline+morphine 20 mg/kg) treatment.

TABLE 3

| Nefiracetam (mg/kg) | Morphine (mg/kg) | N | Withdrawal symptom |
|---|---|---|---|
| (Combined administration group) | | (Jumping) | |
| 0 | 0 | 17 | 0.94 ± 0.67 |
| 5 | 0 | 19 | 0.79 ± 0.79 |
| 10 | 0 | 19 | 0.00 ± 0.00 |
| 0 | 6 | 18 | 11.39 ± 3.23 |
| 5 | 6 | 18 | 1.72 ± 1.37 b |
| 10 | 6 | 18 | 2.61 ± 1.27 b |
| 0 | 20 | 18 | 13.94 ± 3.82 a |
| 5 | 20 | 18 | 8.50 ± 3.79 |
| 10 | 20 | 18 | 4.00 ± 1.61 |
| (Combined administration group) | | (Wet dog shake) | |
| 0 | 0 | 17 | 0.18 ± 0.13 |
| 5 | 0 | 19 | 0.53 ± 0.25 |
| 10 | 0 | 19 | 0.32 ± 0.13 |
| 0 | 6 | 18 | 2.06 ± 0.80 |
| 5 | 6 | 18 | 1.89 ± 0.83 |
| 10 | 6 | 18 | 2.17 ± 0.56 |
| 0 | 0 | 18 | 1.39 ± 0.52 |
| 5 | 20 | 18 | 0.94 ± 0.31 |
| 10 | 20 | 18 | 1.22 ± 0.52 |
| (Combined administration group) | | (Loss of body weight) | |
| 0 | 0 | 17 | −0.21 ± 0.10 |
| 5 | 0 | 19 | −0.21 ± 0.08 |
| 10 | 0 | 19 | −0.08 ± 0.04 |
| 0 | 6 | 18 | −1.11 ± 0.21 aa |
| 5 | 6 | 18 | −0.42 ± 0.11 bb |
| 10 | 6 | 18 | −0.44 ± 0.11 b |
| 0 | 20 | 18 | −0.97 ± 0.15 aa |
| 5 | 20 | 18 | −0.83 ± 0.20 |
| 10 | 20 | 18 | −0.72 ± 0.13 |
| (Combined administration group) | | (Diarrhea) | |
| 0 | 0 | 17 | 0.24 ± 0.14 |
| 5 | 0 | 19 | 0.05 ± 0.05 |

TABLE 3-continued

| Nefiracetam (mg/kg) | Morphine (mg/kg) | N | Withdrawal symptom |
|---|---|---|---|
| 10 | 0 | 19 | 0.00 ± 0.00 |
| 0 | 6 | 18 | 1.39 ± 0.18 aa |
| 5 | 6 | 18 | 0.50 ± 0.17 bb |
| 10 | 6 | 18 | 0.44 ± 0.17 b |
| 0 | 20 | 18 | 1.44 ± 0.15 aa |
| 5 | 20 | 18 | 0.78 ± 0.21 c |
| 10 | 20 | 18 | 0.83 ± 0.20 |

In the groups repeatedly administered with morphine, jumping symptom was increased dose-dependently with morphine administration. In the group administered with 6 mg/kg morphine, the above symptom was inhibited by the pre-treatment with the medicament of the present invention (5 and 10 mg/kg). In the group administered with 20 mg/kg morphine, a tendency was observed that the development of dependency was inhibited dose-dependently with the administration of the medicament of the present invention. In addition, as to wet dog shake, a tendency of the increase of the symptom was observed in the group administered with morphine, although no statistical difference was observed as compared to the control group due to a small numerical numbers of the observed symptoms.

Diarrhea was enhanced in the groups repeatedly administered with morphine. However, significant inhibition of the enhancement of diarrhea was achieved in the group administered repeatedly with 6 mg/kg morphine which was pre-treated with the medicament of the present invention (5 and 10 mg/kg). Furthermore, in the group administered with 20 mg/kg morphine, the enhancement of diarrhea was significantly inhibited by the pre-treatment with the medicament of the present invention (5 mg/kg). As to the loss body weight, significant body weight losses were observed in the groups administered repeatedly with morphine. However, the loss of body weight was inhibited in the group administered with 6 mg/kg morphine which was pre-treated with the medicament of the present invention (5 and 10 mg/kg). A tendency was observed in the group administered with 20 mg/kg morphine that the developments of dependency was inhibited dose-dependently with the administration of the medicament of the present invention.

Industrial Applicability

The medicament of the present invention is useful because the medicament has inhibitory activities against the development of dependency and the development of tolerance to analgesic action induced by the administration of a narcotic analgesic agent.

What is claimed is:

1. A method of at least one of inhibiting development of dependency induced by a narcotic analgesic agent and inhibiting development of tolerance to analgesic action induced by a narcotic analgesic agent, comprising:

administering a narcotic analgesic agent;

administering at least one of a therapeutically effective amount and a preventively effective amount of a medicament to at least one of inhibit development of dependency induced by the narcotic analgesic agent and inhibit development of tolerance to analgesic action induced by the narcotic analgesic agent; and wherein the medicament comprises an active ingredient represented by the following formula: $R^2$-$CH_2$CONH-$R^1$ wherein $R^1$ represents a pyridyl group, a substituted pyridyl group, phenyl group, or a substituted phenyl group; and $R^2$ represents 2-oxo-1-pyrrolidinyl group which may optionally be substituted.

2. The method of claim 1, wherein the at least one of inhibiting development of dependency induced by the narcotic analgesic agent and inhibiting development of tolerance to analgesic action induced by the narcotic analgesic agent comprises inhibiting the development of dependency induced by the narcotic analgesic agent and inhibiting the development of tolerance to analgesic action induced by the narcotic analgesic agent.

3. The method of claim 1, wherein the at least one of inhibiting development of dependency induced by the narcotic analgesic agent and inhibiting development of tolerance to analgesic action induced by the narcotic analgesic agent comprises inhibiting the development of dependency induced by the narcotic analgesic agent.

4. The method of claim 1, wherein the at least one of inhibiting development of dependency induced by the narcotic analgesic agent and inhibiting development of tolerance to analgesic action induced by the narcotic analgesic agent comprises inhibiting the development of tolerance to analgesic action induced by the narcotic analgesic agent.

5. The method of claim 1, wherein the medicament has a prophylactic effect to at least one of:

reduce or prevent the development of dependency induced by the narcotic analgesic agent, and reduce or prevent the development of tolerance to analgesic action induced by the narcotic analgesic agent.

6. The method of claim 1, wherein the medicament has a therapeutic effect to at least one of:

reduce or eliminate dependency already developed by the narcotic analgesic agent, and reduce or eliminate tolerance to analgesic action already developed by the narcotic analgesic agent.

7. The method of claim 1, wherein the active ingredient comprises N-(2,6-dimethylphenyl)-2-(2-oxo-1-pyrrolidinyl) acetamide.

8. The method of claim 1, wherein the narcotic analgesic agent is one of morphine hydrochloride and morphine nitrate.

9. The method of claim 1, wherein the medicament comprises a pharmaceutical composition comprising the active ingredient together with at least one pharmaceutical additive.

10. The method of claim 1, wherein the administering of the medicament is carried out during administration of the narcotic analgesic agent.

11. The method of claim 1, wherein the administering of the medicament is carried out before administration of the narcotic analgesic agent.

12. The method of claim 1, wherein the administering of the medicament is carried out after administration of the narcotic analgesic agent.

13. The method of claim 1, wherein the narcotic analgesic agent is administered at a dosage of about 10 to 30 mg per day from once to three times a day.

14. The method of claim 1, wherein the medicament is administered at a dosage of from 200 to 2000 mg per day, based on weight of the active ingredient.

15. The method of claim 1, wherein the medicament is administered at a dosage of from 300 to 900 mg per day, based on weight of the active ingredient.

16. The method of claim 1, wherein the narcotic analgesic agent is administered at a dosage of about 10 to 30 mg per day from once to three times a day, and wherein the medicament is administered at a dosage of from 200 to 2000 mg per day, based on weight of the active ingredient.

17. The method of claim 1, wherein the medicament is administered at a dosage of from 200 to 2000 mg per day, based on weight of the active ingredient, and wherein the medicament is administered at a dosage of from 300 to 900 mg per day, based on weight of the active ingredient.

18. The method of claim 1, wherein $R^1$ represents substituted pyridyl group, and wherein the substituted pyridyl group comprises at least one substituent selected from the group consisting of halogen atom, trifluoromethyl group, nitro group, acetyl group, alkyl group, alkoxy group, alkylmercapto group, amino group, sulfonyl group, and aminoethoxycarbonyl group.

19. The method of claim 1, wherein $R^1$ represents substituted phenyl group, and wherein the substituted phenyl group comprises at least one substituent selected from the group consisting of halogen atom, trifluoromethyl group, nitro group, acetyl group, alkyl group, alkoxy group, alkylmercapto group, amino group, sulfonyl group, and aminoethoxycarbonyl group.

20. The method of claim 1, wherein the narcotic analgesic agent comprises an alkaloid.

21. The method of claim 1, wherein the narcotic analgesic agent comprises an analgesic peptide.

22. A method of at least one of inhibiting development of dependency induced by a narcotic analgesic agent and inhibiting development of tolerance to analgesic action induced by a narcotic analgesic agent in a patient who has been administered a narcotic analgesic agent, comprising:

administering at least one of a therapeutically effective amount and a preventively effective amount of a medicament to at least one of inhibit development of dependency induced by the narcotic analgesic agent and inhibit development of tolerance to analgesic action induced by the narcotic analgesic agent; and wherein the medicament comprises an active ingredient represented by the following formula: $R^2$-$CH_2$CONH-$R^1$ wherein $R^1$ represents a pyridyl group, a substituted pyridyl group, phenyl group, or a substituted phenyl group; and $R^2$ represents 2-oxo-1-pyrrolidinyl group which may optionally be substituted.

23. The method of claim 22, wherein the active ingredient comprises N-(2,6-dimethylphenyl)-2-(2-oxo-1-pyrrolidinyl) acetamide.

24. The method of claim 22, wherein the narcotic analgesic agent is one of morphine hydrochloride and morphine nitrate.

25. The method of claim 22, wherein the medicament is administered at a dosage of from 200 to 2000 mg per day, based on weight of the active ingredient.

26. The method of claim 22, wherein the medicament is administered at a dosage of from 300 to 900 mg per day, based on weight of the active ingredient.

* * * * *

UNITED STATES PATENT AND TRADEMARK OFFICE
CERTIFICATE OF CORRECTION

PATENT NO. : 6,107,330
DATED : August 22, 2000
INVENTOR(S) : T. HABESHIMA et al.

It is certified that error appears in the above-identified patent and that said Letters Patent is hereby corrected as shown below:

On the cover of the printed patent, at Item [22], PCT Filed Date, change "Aug. 6, 1995" to --- Aug. 6, 1996---.

Signed and Sealed this

First Day of May, 2001

Attest:

NICHOLAS P. GODICI

*Attesting Officer*       *Acting Director of the United States Patent and Trademark Office*